(12) United States Patent
Elliot

(10) Patent No.: US 10,247,545 B2
(45) Date of Patent: Apr. 2, 2019

(54) LASER GAUGE FOR ROBOTIC CALIBRATION AND MONITORING

(71) Applicant: THINK SURGICAL, INC., Fremont, CA (US)

(72) Inventor: Gibson Elliot, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 0 days.

(21) Appl. No.: 15/549,485

(22) PCT Filed: Feb. 12, 2016

(86) PCT No.: PCT/US2016/017796
§ 371 (c)(1),
(2) Date: Aug. 8, 2017

(87) PCT Pub. No.: WO2016/130946
PCT Pub. Date: Aug. 18, 2016

(65) Prior Publication Data
US 2018/0023946 A1      Jan. 25, 2018

Related U.S. Application Data

(60) Provisional application No. 62/161,708, filed on May 14, 2015, provisional application No. 62/116,191, filed on Feb. 13, 2015.

(51) Int. Cl.
  *G01B 11/14* (2006.01)
  *G01B 11/24* (2006.01)
  (Continued)

(52) U.S. Cl.
  CPC .......... *G01B 11/2433* (2013.01); *A61B 34/20* (2016.02); *A61B 34/32* (2016.02);
  (Continued)

(58) Field of Classification Search
  CPC ... G01B 11/2433; G01B 11/002; A61B 34/30; A61B 34/32; A61B 17/1668;
  (Continued)

(56) References Cited

U.S. PATENT DOCUMENTS 4,791,759 A * 12/1988 Komata ................. B24B 49/14
                                                                  451/21
5,086,401 A    2/1992 Glassman et al.
(Continued)

FOREIGN PATENT DOCUMENTS

EP    1584426 A1    10/2005
EP    2023844 A2     2/2009
(Continued)

OTHER PUBLICATIONS

Beasley, Ryan A., "Medical Robots: Current Systems and Research Directions", Journal of Robotics, Jul. 2012, pp. 1-14, vol. 2012, Hindawi Publishing Corporation, Copyright Ryan A. Beasley (2012).
(Continued)

*Primary Examiner* — Sunghee Y Gray
(74) *Attorney, Agent, or Firm* — Avery N. Goldstein; Blue Filament Law PLLC

(57) ABSTRACT

A contactless, and accurate device and methods of use thereof are provided to calibrate and verify the calibration of a robotic arm and associated attachments. The device uses a laser gauge for calibrating and subsequently verifying the calibration of the robotic arm, digitizer, or robotic tools. An optical transmitter, in communication with an optical receiver is fixed nearly perpendicular to a second optical transmitter in communication with a second optical receiver that form two optical micrometers that are offset a small distance, forming a small gap, d, to create a measuring void having two distinct non-intersecting measurement planes. One measurement plane measures the position and size of an
(Continued)

object in a first axis direction and the other measurement plane measures the position and size of an object in a second axis direction. The position and size of an object is measured within the measuring void in both axial directions.

9 Claims, 8 Drawing Sheets

(51) Int. Cl.

| | | |
|---|---|---|
| *G01B 11/00* | (2006.01) | |
| *A61B 34/20* | (2016.01) | |
| *A61B 34/32* | (2016.01) | |
| *B25J 9/16* | (2006.01) | |
| *A61B 34/30* | (2016.01) | |
| *A61B 17/00* | (2006.01) | |
| *A61B 17/16* | (2006.01) | |
| *A61B 90/00* | (2016.01) | |

(52) U.S. Cl.
CPC ........... *B25J 9/1692* (2013.01); *G01B 11/002* (2013.01); *A61B 17/1668* (2013.01); *A61B 34/30* (2016.02); *A61B 2017/00725* (2013.01); *A61B 2034/2057* (2016.02); *A61B 2090/0812* (2016.02); *G05B 2219/45117* (2013.01)

(58) Field of Classification Search
CPC .......... A61B 34/20; A61B 2017/00725; A61B 34/10; A61B 17/16; A61B 2034/2057; A61B 2090/0812
USPC ....................................................... 356/614
See application file for complete search history.

(56) References Cited

U.S. PATENT DOCUMENTS

| | | | |
|---|---|---|---|
| 5,400,638 A * | 3/1995 | Kim | ........................ B25J 9/1692 |
| | | | 73/1.79 |
| 5,408,409 A | 4/1995 | Glassman et al. | |
| 6,643,565 B2 | 11/2003 | Manes et al. | |
| 8,180,487 B1 | 5/2012 | Vangal-Ramamurthy et al. | |
| 8,287,522 B2 | 10/2012 | Moses et al. | |
| 8,469,947 B2 | 6/2013 | Devengenzo et al. | |
| 2010/0141965 A1* | 6/2010 | Schneider | ............. B24B 47/225 |
| | | | 356/621 |
| 2011/0043803 A1 | 2/2011 | Nygaard et al. | |
| 2014/0288710 A1 | 9/2014 | Ikenaga et al. | |
| 2015/0277398 A1* | 10/2015 | Madvil | .................. G05B 13/04 |
| | | | 700/97 |

FOREIGN PATENT DOCUMENTS

| | | |
|---|---|---|
| JP | 2005059103 A | 3/2005 |
| WO | 9709929 A1 | 3/1997 |
| WO | 2014042668 A2 | 3/2014 |

OTHER PUBLICATIONS

International Search Report dated May 10, 2016 for International Application No. PCT/US2016/017796 filed Feb. 12, 2016.
European Search Report dated Jun. 27, 2018 for European Application No. 16749982 filed Feb. 12, 2016.

* cited by examiner

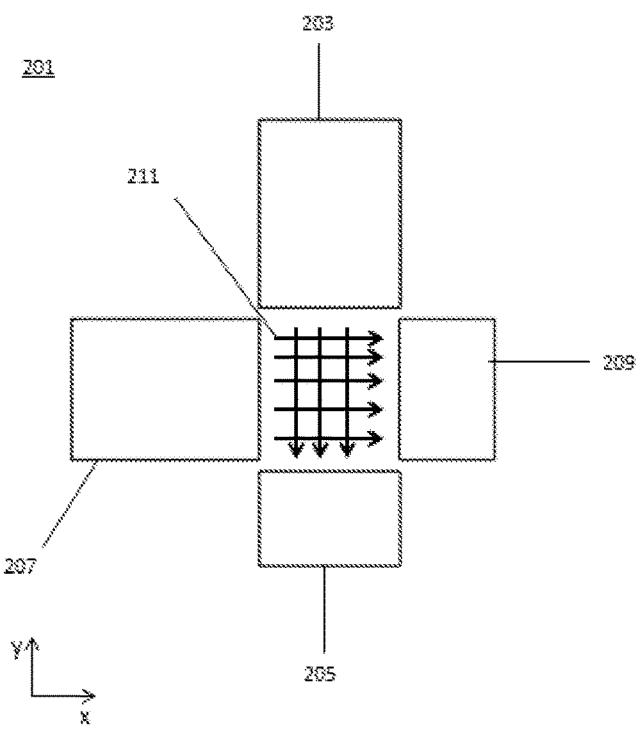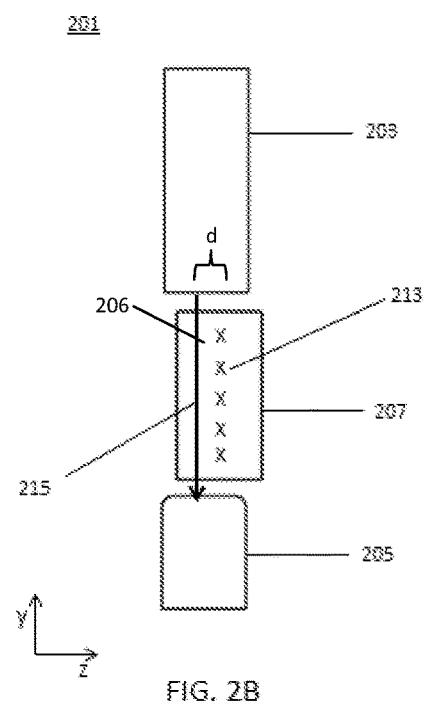
FIG. 2A
FIG. 2B

LASER GAUGE FOR ROBOTIC CALIBRATION AND MONITORING

CROSS REFERENCE TO RELATED APPLICATIONS

This application claims priority benefit of U.S. Provisional Application Ser. No. 62/161,708 filed 14 May 2015, and U.S. Provisional Application Ser. No. 62/116,191 filed 13 Feb. 2015; the contents of which are hereby incorporated by reference.

FIELD OF THE INVENTION

The present invention generally relates to the field of computer-aided surgical systems, and more specifically to a new and useful device and method to verify the calibration of a robotic arm and robotic tools to perform total joint arthroplasty.

BACKGROUND OF THE INVENTION

Autonomous computer-aided surgical systems generally consist of a robotic arm attached to a base. The robotic arm performs a set of instructions created either pre-operatively or intra-operatively to aid the user in performing a particular medical procedure. One such system is the ROBODOC™ Surgical System (THINK Surgical, Fremont, Calif.) that aids a user in precisely milling the cavity of a femur to receive an implant in total hip arthroplasty (THA). As shown in FIGS. 1A and 1B the ROBODOC™ Surgical System 101 generally consists of a robotic base 103, a robotic arm consisting of various links and joints 105, a tool 107 having a tool tip 108, and a digitizer 109. The digitizer 109 is a passive mechanical arm having a digitizer probe with a probe tip 110. The digitizer 109 is used to collect a set of points on a bone to register the bone coordinate frame with the robots coordinate frame.

In order to ensure that a bone cavity is created with sub-millimeter accuracy, the robotic arm, digitizer 109, and tools all need to be within tight operating parameters. Generally, the robotic arm and digitizer 109 are calibrated by the manufacturer when first installed at a customer's site. The kinematic parameters are updated to account for any errors including joint-level errors, kinematic modelling errors, and non-geometric errors. Subsequently, prior to each medical procedure, the calibration is verified to ensure the accuracy of the system.

Many different external measuring devices and methods are used to calibrate or verify the calibration of a robotic arm including touching the tool tip to reference parts, laser triangulation, and calipers. As many of these techniques have been employed on industrial robots, their use in computer-aided surgical systems is limited due to the surgical setting and strict regulatory requirements. For example, the ROBODOC™ Surgical System utilizes a reference plate. The reference plate has multiple reference points that are spaced a known distance apart within very tight tolerances. The tool tip 108 and digitizer tip 109 are guided to the center of each of the reference points. The position of the digitizer tip 110 and tool tip 108 is recorded at each of these reference points using the kinematics (e.g., Denavit-Hartenberg (DH) parameters, encoder values) of the digitizer 109 or robot 101. If the difference between the known locations of the reference points is within a specified tolerance of what is measured by the kinematics, then the calibration of the robot and digitizer is verified. The procedural steps are often time consuming and require additional hardware (i.e., reference parts, calibration probes, optical tracking systems) that can further increase costs. Additionally, when verifying calibration prior to surgery, the external measuring tools must be sterile; this results in increased disposables and/or sterilization considerations.

Additionally, surgical systems often require maintenance and tuning to ensure the operating parameters are functioning properly. However, maintenance is usually only performed at designated time intervals or when there is a noticeable error or system malfunction.

Thus there exists a need in computer-aided surgical systems for a quick method to calibrate and verify the robot and robotic tools are calibrated. There further exists a need to maintain the sterile environment during calibration verification. There is an even further need to provide feedback to a user when to tune or provide maintenance to a surgical system prior to a malfunction

SUMMARY OF THE INVENTION

A laser gauge for calibration of a robotic arm and associated attachments includes a first micrometer in communication with a first receiver, and a second micrometer in communication with a second receiver, where the first micrometer is offset from the second micrometer to create a measurement void with two non-intersecting measurement planes in a space defined between the first micrometer and the first receiver and between the second micrometer and the second receiver. The two non-intersecting measurement planes form a first plane that measures a first position and size of an object in a 'y' axis direction and a second plane that measures a second position and size of the object in a 'x' axis direction, where the position and size of the object is measured within the measuring void in both the 'x' axis direction and 'y' axis direction.

A method for verifying calibration of a robotic arm with the laser gauge taught herein includes performing an initial calibration of the robotic arm by passing an end effector of the robotic arm through the measurement void formed between the first and second micrometers at least once, and recording and storing from the first micrometer and the second micrometer a position of the end effector within the measuring void. The recorded position of the end effector from the initial calibration procedure is used as a comparison tool to verify the robotic arm calibration in a subsequent calibration procedure.

BRIEF DESCRIPTION OF THE DRAWINGS

The present invention is further detailed with respect to the following drawings that are intended to show certain aspects of the present invention, but should not be construed as a limit on the practice of the present invention.

FIGS. 2A and 2B are a front and side view of a laser gauge in accordance with embodiments of the invention;

DETAILED DESCRIPTION OF THE INVENTION

The present invention has utility as a user-friendly, fast, contactless, and accurate device and methods to calibrate and verify the calibration of a robotic arm used in medical procedures. The following description of various embodiments of the invention is not intended to limit the invention to these specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of the range. By way of example, a recited range from 1 to 4 is intended to include 1-2, 1-3, 2-4, 3-4, and 1-4.

As used herein, the term 'communication' is used to refer to the sending or receiving of data or energy either through a wireless or electrical connection unless otherwise specified. Such 'communication' maybe accomplished be means well known in the art such as Ethernet cables, BUS cables, Wi-Fi, WLAN, Bluetooth, and the like. The 'communication' may also be accomplished using visible light as described in U.S. Prov. Pat. App. Nos. 62/083,052 and 62/111,016 which are both hereby incorporated by reference in their entirety.

Figure 1A:
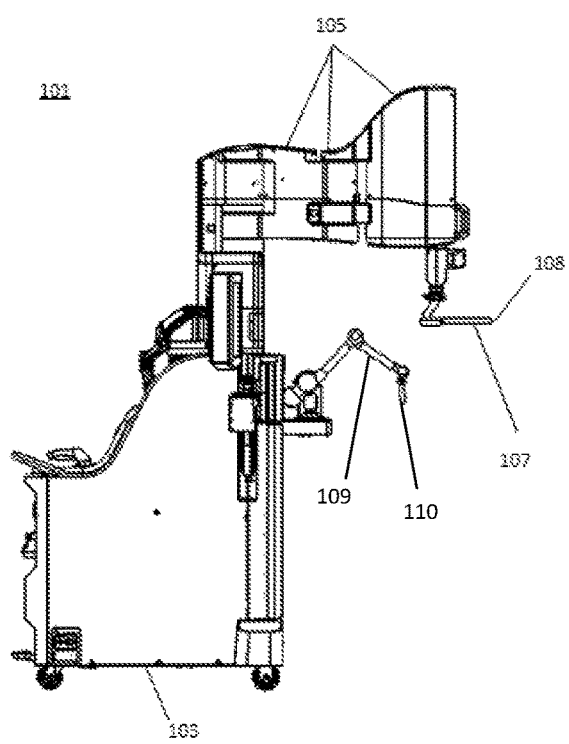
FIGS. 1A and 1B are a side and front view of the ROBODOC™ Surgical System main components.
Figure 1B:
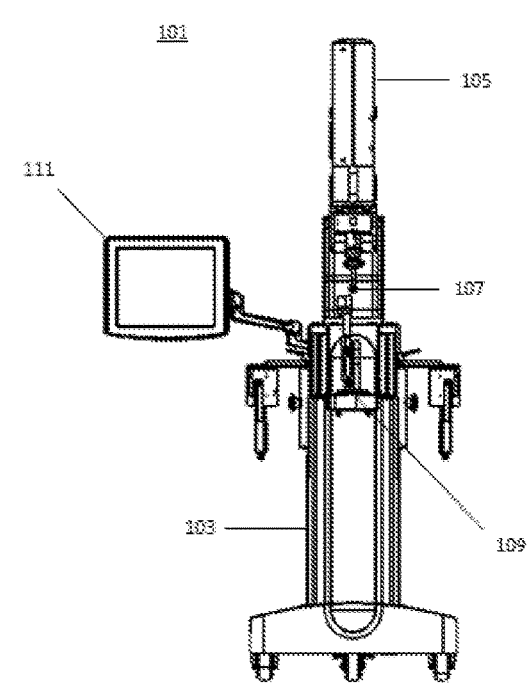

As reference will be made to the ROBODOC™ Surgical System, it should be appreciated that any autonomous, semi-autonomous robotic system either for medical or industrial applications can benefit from the device and methods disclosed herein. In the context of the description, a robotic system as exemplified in FIG. 1 has a base 103 with various links connected by revolute and/or prismatic joints 105 to manipulate an end-effector or tool 107 to perform a certain function. The 'tool' can be any instrument actively, semi-actively, passively, haptically, and/or manually manipulated through at least one link and joint (i.e., robotic arm, digitizer). The 'tool' may be, for example, a probe, a ball cutter, a flat cutter, a drill bit, a saw, a blade, or a burr. The tool 107 may have a tool tip 108 for contacting or doing work on a workpiece. The robotic system 101 may include a user interface such as a monitor 111 to display user instructions, operating parameters, procedural workflow, the robotic state, functioning errors, guide commands, and display the real-time position of the tool 107 with respect to the workpiece. The user interface may also be for example a heads up display unit (HUD), Google glasses, a smart phone, and/or a smart watch which may be in communication with the robotic system. A user may interact or interface with the robotic system through the use of an input mechanism illustratively including a joystick, mobile phone, a pendant, mouse, keyboard, foot pedal, or by touching the monitor 111. Such inputs may illustratively include for example guide commands, selecting various prompts given throughout a procedural workflow, selecting a certain medical procedure, designating the position of other external components/devices, aiding in registration of anatomy, configuring an optical tracking system, as well as any other inputs required before, during, and/or after a medical procedure.

More detailed descriptions of such robotic systems and their applications can be found in U.S. Pat. Nos. 5,086,401, 8,287,522, WO 19/97009929, U.S. Pat. Nos. 5,408,409, and 8,469,947. Further descriptions of such robotic systems can also be found in the literature, including: Beasley, R. "Medical Robots: Current Systems and Research Directions," Journal of Robotics, Volume 2012, July 2012.

The device and methods disclosed herein additionally refer to the use of optical micrometers. The term 'optical micrometer' refers to an optical transmitting device in communication with an optical receiver spaced a distance apart to create a measuring void. The optical micrometer is capable of measuring the size and location of an object within the measuring void. Non-limiting illustrative examples of optical micrometers include the IG series Multi-Purpose CCD Laser Micrometer and IB series Laser Thrubeam™ Sensor (Keyence, Itasca, Ill.). The optical transmitting device emits electromagnetic radiant energy such as ultraviolet, visible light, or infrared energy, which is also referred to herein as an optical emission. However, it should be appreciated that other forms of energy can be emitted and used to detect the position and/or size of an object other than optical energy illustratively including ultrasound or magnetism. The receivers may similarly be any corresponding detecting device such as photodiodes, CCD cameras, CMOS cameras, magnetic field sensor, transducers and the like.

Laser Gauge

Referring now to the figures, FIGS. 2A and 2B are a front and side view of a laser gauge 201 in accordance with embodiments of the invention. The laser gauge 201 may be used to provide various methods for calibrating and subsequently verifying the calibration of a robotic arm, digitizer, or robotic tools. An optical transmitter 203, in communication with an optical receiver 205 is fixed nearly perpendicular to a second optical transmitter 207 in communication with a second optical receiver 209. The two optical micrometers create a measuring void 211 having two measurement planes 213 and 215. One measurement plane 213 measures the position and size of an object in a first axis direction (e.g., 'y' axis direction) and the other measurement plane 215 measures the position and size of an object in a second axis direction (e.g., 'x' axis direction). Therefore, the position and size of an object can be measured within the measuring void 211 in both the 'x' axis direction and 'y' axis direction. As seen in FIG. 2B, the optical micrometers are offset a small distance, d, to create a small gap 206 between the two measuring planes 213 and 215. Therefore, the laser gauge has two distinct non-intersecting measuring planes. With this gap, various methods and/or mathematical operations can be programmed with the robot computer to obtain additional information about the position, size and/or orientation of the robotic arm or robotic tool 107.

Figure 3:
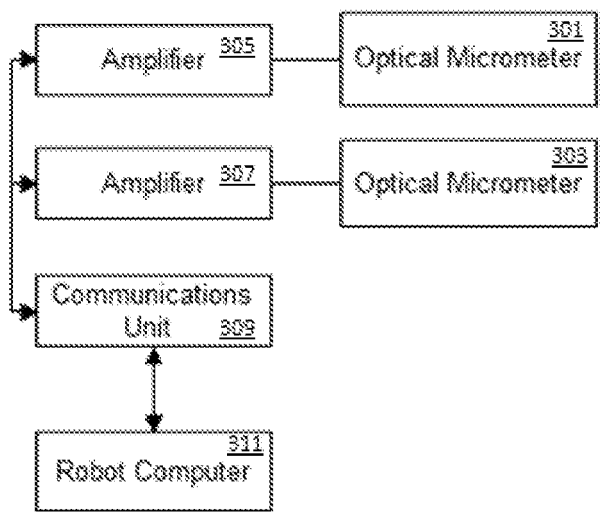
FIG. 3 is a schematic block diagram of the connections of the optical micrometers with the robotic computer in accordance with embodiments of the invention.

In a specific inventive embodiment, with respect to FIG. 3, the optical micrometers 301 and 303 are in communication with amplifiers 305 and 307, respectively. The amplifiers 305 and 307 are connected to a communications unit 309 that is in communication with the robot computer 311. The robot computer 311 may be any of a robot control computer, a real-time monitoring computer, a processor, a controller, and/or any combination of hardware, software and/or firmware. The robotic system 101 may consist of a single robot computer or have multiple robot computers in communication with one another. The optical micrometers (301, 303), amplifiers (305, 307), and communications unit 309 may be housed in a casing (not shown) and attached to or integrated with the robot base 103. The robot base 103 may have various attachment points for the laser gauge 201 to accommodate different medical procedures or allow easy access to the measuring void 211. For example, the ROBODOC™ Surgical System is oriented relative to the patient based on the operative side (e.g., left or right femur). The laser gauge 201 may be attached to the base 103 in a position that will easily allow the tool 107 to pass through the measuring void 211 without interfering with other components of the system or other tools in the operating field depending on the medical procedure. The robot computer is further programmed with the general coordinates (within a few millimeters) of the measuring void 211 at each attachment point on the robot base 103.

The laser gauge 201 may also be incorporated or fixed to the robot 101. For example, the laser gauge 201 may be manufactured at a defined position within the robot base 103. The robot computer 311 may be programmed with the specific location of the laser gauge 201. The location of the laser gauge 201 may also be updated or adjusted in the robot computer 311 manually by a user post-manufacture.

Depth Gauge

To ensure the optical micrometers are accurately measuring the correct coordinates and size of an object as it passes through the measuring void 211, a laser gauge calibration procedure may be performed. Any coordinate measuring machine used in a medical application is subject to a calibration standard. During the manufacture of the laser gauge 201, the two measuring planes may not be fixed exactly perpendicular to one another, nor will the distance, d, of the gap 206 between the two planes always be the same. Therefore, the accuracy of the micrometer measurements, and the angular offset and distance, d, between the planes needs to be determined prior to use.

Figure 6A:
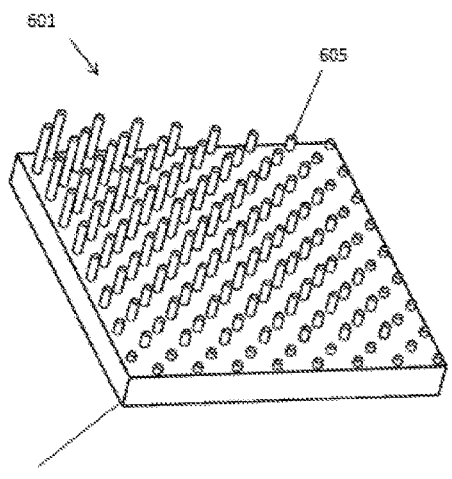
FIGS. 6A and 6B illustrate two configurations of a depth gauge in perspective views in accordance with embodiments of the invention.

In a specific inventive embodiment, the distance between the two planes may be measured using a depth gauge 601 illustratively shown in FIG. 6A. Pins 605 of varying height are configured on a plate 603 where the pin heights and locations are manufactured within tight tolerances. The height and pin locations may be further verified and validated through additional procedures known in the art (e.g., a coordinate measuring machine). The outer dimensions of the plate 603 may be manufactured to the outer dimensions of the laser gauge 201 to allow the depth gauge 601 to easily insert or attach thereto. To measure the distance, d, of the gap 206 between the planes, the plate 603 is assembled to the measuring void 211. Some of the pins 605 will be measured in both measuring planes. Because the pin locations and heights are known with respect to one another on the plate 603, the pin(s) having the shortest height that crosses both planes indicate the distance, d, of the gap 206. The distance, d, of the gap may vary within the measuring void 211 and can be determined accordingly due to the known configuration of the pins 605 and the corresponding coordinates measured in the measuring void 211. The known gap distance, d, may be used for calibration and calibration verification as further described below.

Figure 6B:
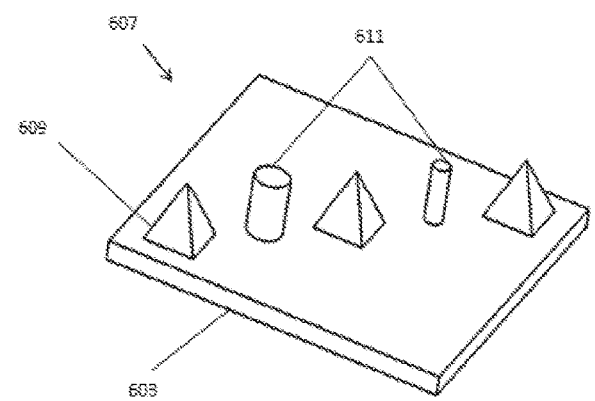

With respect to FIG. 6B, a depth gauge 607 may be configured with pyramid 609 and/or cone like structures. Multiple pyramids 609 or cone like structures may be configured diagonally across the plate such that one pyramid does not obstruct or cast an additive shadow on a second pyramid along a linear path of optical emission. The width of the pyramid is known at any given height of the pyramid based on the manufacturing tolerances and any additional validation procedures (i.e., coordinate measuring machines, calipers) generated post depth gauge 607 manufacture. When the depth gauge 607 is affixed to the laser gauge 201, the width of the pyramid 609 or cone is measured in both the 'x' and 'y' directions. Based on the width measurements, the gap between the two measuring planes can be determined. For example, the 'x' width measurement for one pyramid may be 5 units and the 'y' width measurement may be 3 units. Depending on the known slope of the pyramid, the side angles of the pyramid, or any other geometric information determined in a depth gauge validation procedure (e.g., finding the slope of the cone with a coordinate measuring machine or calipers), the distance, d, of the gap 206 between the measuring planes may be calculated. It should be appreciated that a pyramid 609 or cone like structure with a shallower slope may provide better resolution because the width of the pyramid 609 changes more dramatically with changes in the pyramid 609 height.

To ensure, or to account for any error in the width measurements, cylinders 611 of a known and validated diameter may be incorporated with the plate 603. In a particular embodiment, multiple cylinders may be used with varying diameter. If the 'x' and 'y' width measurements of the cylinder(s) match the validated true diameter, then the optical micrometers are accurate. If the measurements are outside of the true value of the cylinder(s), then the optical micrometers can be calibrated to reduce or eliminate the discrepancy. If the 'x' width measurement and the 'y' width measurement are different, then the two measuring planes may be angularly offset and not perfectly perpendicular in which case one or both micrometers may be calibrated. A ratio, transform or correction factor between the 'x' width measurement and the 'y' width measurement may then be stored to define the angular planar relationship between the two planes for future use.

In the case where the two measuring planes may be angularly offset, then the gap 206 between the two measuring planes may vary depending on where the tool 107 or object is passed through the measuring void 211. However, in a particular inventive embodiment, a reference plane may be created within the gap to be used for the calibration and calibration verification of the surgical system. Because the depth gauges 601, and 607 contain elements 605, and 609, 611, respectively, of varying shapes, physical coordinates, and heights, all x, y and z coordinates may be accounted for. With three x, y and z coordinates, a plane may be defined in three-dimensional space. For example, the depth gauge 607 illustratively includes three pyramids, diagonally placed on the plate 603. When the depth gauge 607 is affixed to the laser gauge 201, one optical micrometer measures three 'x' coordinates, and the other optical micrometer measures three 'y' coordinates. From the pyramid 609 width measurements are used to obtain the gap distance, d, as described previously and/or the location and height of each of the pins 605, three 'z' coordinates may be defined. The three 'z' coordinates may be stored as half of the measured and/or determined gap size, d, that may represent the center between the two measuring planes. From the three sets of coordinates, a plane may be defined within the measuring void 211. The defined plane provides a reference standard that relates the two fixed measuring planes relative to one another. Once the laser gauge 201 is calibrated (i.e., width measurements are accurate, coordinate measurements are accurate, orientation of the planes relative to one another is known and related, gap between the two measuring planes is known) various beneficial procedures may be performed.

Calibration Verification Using Laser Gauge Coordinates

Figure 4:
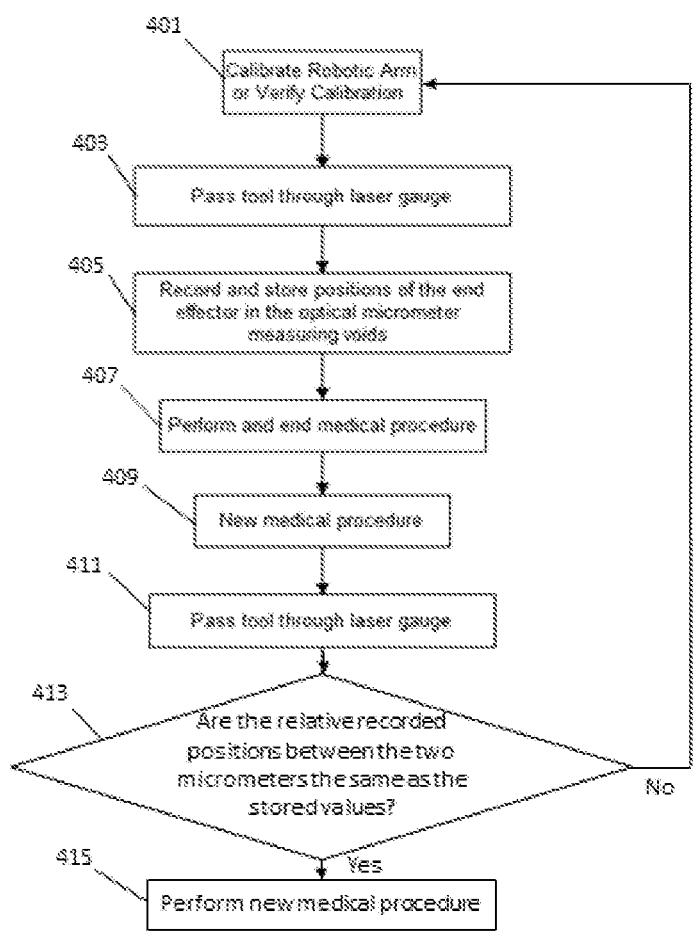
FIG. 4 is a flowchart of a method to verify the calibration of a robotic arm in accordance with embodiments of the invention.

In a specific inventive embodiment, a method for verifying the calibration of a robotic arm is generally shown in FIG. 4. The robotic arm may be initially calibrated using any of the traditional techniques well known in the art illustratively including the reference plate calibration described previously (Block 401). After the initial calibration is complete, the tool 107 is passed through the laser gauge 201 (Block 403). In a specific embodiment, the tool 107 is automatically passed through the laser gauge 201 without active user assistance. The user by way of an input mechanism may designate to the robot computer where the laser gauge 201 is attached on the robotic base 103(e.g., the laser gauge 201 is located on the left or right side of the robotic base 103). In another specific embodiment, the tool 107 may be manually positioned to the laser gauge 201 by a user, such that when the tool 107 is in the approximate location of the measuring void 211, the robot constrains the tool 107 and takes active control to pass the tool 107 through the measuring void 211 autonomously. The robot computer may be pre-programmed with specific joint angles, coordinates, controller velocities, and one or more tool dimensions to pass the tool 107 through the measuring void 211.

Figure 5:
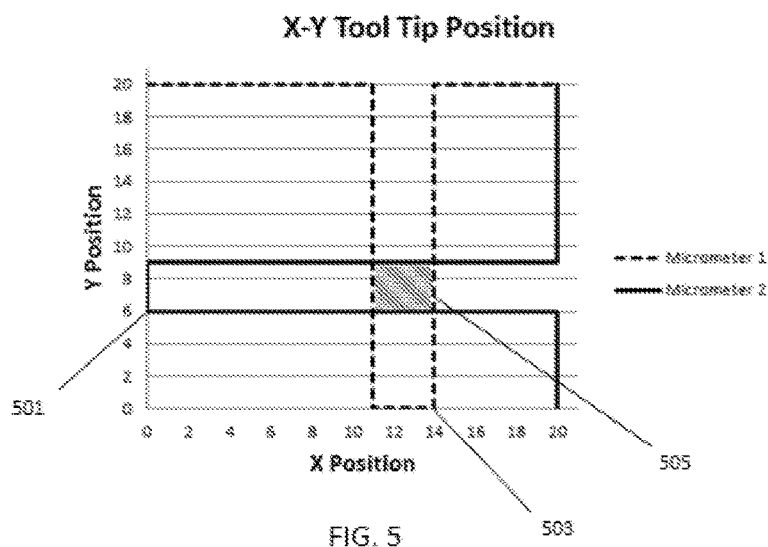
FIG. 5 is an x-y plot of tool tip position as collected by the measuring voids in accordance with embodiments of the invention.

Continuing with the method of FIG. 4, the tool 107 is passed through the measuring void 211 at least three times to collect at least three different points. In a specific inventive embodiment, the tool tip 108 may be spherical in shape consisting of a sphere center. The robot may be programmed to pass the tool 107 through the measuring void 211 at three different points spaced a programmed distance apart. The optical micrometers may measure an 'x' and 'y' position. For example, one point collected by the measuring voids 211 can be seen in FIG. 5. The position and geometry is determined by the micrometers from the absence of optical emission in the 'y' direction as 501 and the 'x' direction as 503. In the illustrative example of FIG. 5, one optical micrometer measures a tool tip 108 position in the 'y' direction as 7.5 and the other optical micrometer measures a tool tip 108 position in the 'x' direction as 12.5 corresponding to a tool tip center point of (12.5, 7.5) in laser gauge coordinates. Two and/or more additional points may be collected by subsequently passing the tool 107 through the laser gauge 201 for at least a total of three points. The relationships between the three points are then calculated by the robot computer. For example, the robot computer may construct a triangle between the points whereby the side lengths and angles of the triangle are calculated. The points and computed relationships are recorded and stored in the robot computer for later use (Block 405).

Following the completion of the first medical procedure (Block 407), typically the robot 101 would need to be re-calibrated or the calibration re-verified using time consuming and costly techniques (i.e., reference points on a reference plate) prior to performing a subsequent procedure (Block 409). However, in embodiments of the inventive method, the tool 107 may be passed through the laser gauge 201 at least three times to collect at least three points (Block 411). As in the first procedure, the robot computer calculates the relationships between the three points, such as a triangle, and the respective side lengths and angles. The robot computer subsequently compares the relationships between the points collected in the first procedure to the relationships of the points collected in the second procedure (decision Block 413). If the relationships between the points match within a certain allowable threshold (decision Block 413 is Yes) then the robot can continue to perform the new medical procedure (Block 415). If the comparison is outside of the threshold (decision Block 413 is No), then the robot needs to be re-calibrated or the calibration re-verified using traditional techniques as in the first procedure (Block 401).

The calculated relationships of the points collected from the first procedure are used as the comparison for any subsequent procedure. A benefit of the laser gauge 201 is that the laser gauge 201 may be re-positioned on the robotic system and still pass calibration verification (Block 413). Since the optical micrometers are fixed relative to each other, the laser gauge coordinate frame remains the same. Therefore as long as the relationships between the points collected within the measuring void 211 in subsequent procedures matches the relationships of the points calculated in the first procedure, the calibration remains accurate. For example, in the first procedure the robot computer calculates a first point (2, 4), a second point (3, 5) and a third point (4, 3) in three dimensional space. The side length and angles between the points may be calculated. If in the subsequent procedure the robot computer calculates a first point (3, 5), a second point (4, 6) and a third point (5, 4), the side lengths and angles between the points still match the first procedure. Since the robot is programmed to pass through the measuring void 211 of the laser gauge 201 at three distinct points at known distances and angles from each other, the robot is still accurate regardless of the coordinates measured by the optical micrometers. The laser gauge 201 provides a quick and easy verification tool to ensure the robot is within the operating parameters. Thus, the need to perform a recalibration (Block 401) with a traditional technique is eliminated and the next surgical procedure can commence saving significant operating time.

Figure 7:
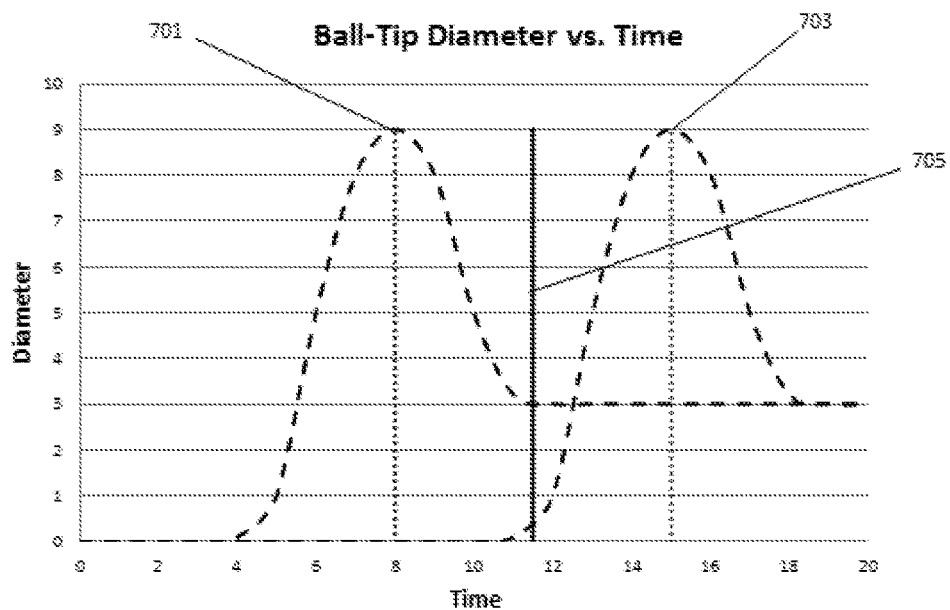
FIG. 7 is a plot of measuring spherical-tip diameter as a function of time in accordance with an embodiment of the invention.

In a specific embodiment of the inventive method, a tool tip 108 with the shape of a sphere may be attached to the end of the robotic arm. The center of the sphere may be determined by the measuring void 211 as depicted in FIG. 7. As the tool tip 108 passes through the two optical micrometers as a function of time, the profile of the sphere is measured. For example, as the tool tip 108 passes through the first optical micrometer, the profile of the sphere in the 'x' direction will be captured until it reaches a maximum value 701, which represents the diameter of the sphere in that respective direction. As the tool 107 keeps passing through the measuring void 211, it will reach the next measuring plane where the tool tip profile is again captured. The maximum value 703 in the second measuring plane represents the diameter of the sphere in the 'y' direction. Half of the maximum values in both directions can be calculated to determine the center point of the sphere or in this case the center point of the tool tip 108. This may be necessary to determine and verify the exact location of the center point of the tool tip 108 for calibration. Again, the method outlined in FIG. 4 may be followed wherein three tool center points may be collected. Therefore, it is assured that center point of the tool tip 108 is being measured for the first and every subsequent procedure. A plane in the center of the two planes 705 may also be determined by using the distance, d, of the gap 206 measured from the depth gauge 601, 607 or by knowing the velocity of the arm and the diameter of the tool tip 108 as it is passed through the measuring void 211.

In a specific inventive embodiment, the tool 107 may be passed into the measuring void 211 wherein the robot is programmed to move the tool 107 in a specific shape. For example, the tool 107 is placed within the measuring void 211 wherein the robot computer is programmed to trace a shape of a known dimension, such as an arc, circle, ellipse, triangle, or square. The 'x' and 'y' positions of the tool 107 are measured during the tracing where the robot computer may calculate or fit a model to the shape. Further, the robot computer may calculate normal vectors to the shape to be used as the comparative relationship for subsequent procedures. For example, if the diameter of the traced circle in the first procedure matches the diameter of the traced circle in any subsequent procedure (Block 413) then the new procedure can commence (Block 415).

In specific inventive embodiments, other information measured by the optical micrometers may be used for additional calibration verification. For example, the robot computer may use the method of FIG. 4 while the optical micrometers additionally measure the tool geometry (i.e., a cylindrical tool, the diameter of the tool, a spherical tool) as an additional verification check. The tool geometry may also provide information related to the orientation of the tool within the measuring void 211. If in a first procedure the size of the tool 107 is measured as 4 units and a subsequent procedure measures a size of 4.5 units, then the tool 107 may be oriented so that it obstructs additional optical emission to the receiver, which may be an indication that the robot is no longer within its operating parameters. Even if the two measuring planes are angularly offset, the calibration procedure with the depth gauges 601 and 607 has accounted for this mismatch and can therefore accurately determine if a tool or object is at a certain angle. The tool 107 may be further articulated by the robot 101 to match the actual diameter of the tool 107 such that the calibration may be further verified (see Calibration Verification with an Unexpectedly Oriented Tool below).

In a specific inventive embodiment, a time or use stamp may be associated with the initial robot calibration or calibration verification (Block 401). The time or use stamp ensures that the robot is calibrated or the calibration is verified using traditional techniques (e.g., reference plate) after so many procedures or after a specified time has elapsed. For example, if it shown that after ten surgical procedures that the relationships of the points collected is no longer within the tolerance of the initial procedure, the time or use stamp may be set at nine procedures to cause the user to re-calibrate or verify calibration of the robot (Block 401). The method of FIG. 4 may then be repeated until the time or use stamp expires again.

Calibration Verification Using Laser Gauge Coordinates and Robotic Coordinates

Another calibration may be performed using both the laser gauge coordinate system and the robotic system coordinate system. In general, the two optical micrometers have a fixed relationship and therefore have their own laser gauge coordinate system. The accuracy of the laser gauge coordinates may be calibrated with the depth gauges 601 and 607 as previously described. The data collected from the optical micrometers may be processed with the robot computer or the laser gauge 201 may have a separate computer/controller in communication with the robot computer. For simplicity, the robot computer or laser gauge computer/controller will be referred to hereafter as the hardware/software unless otherwise specified.

Figure 9:
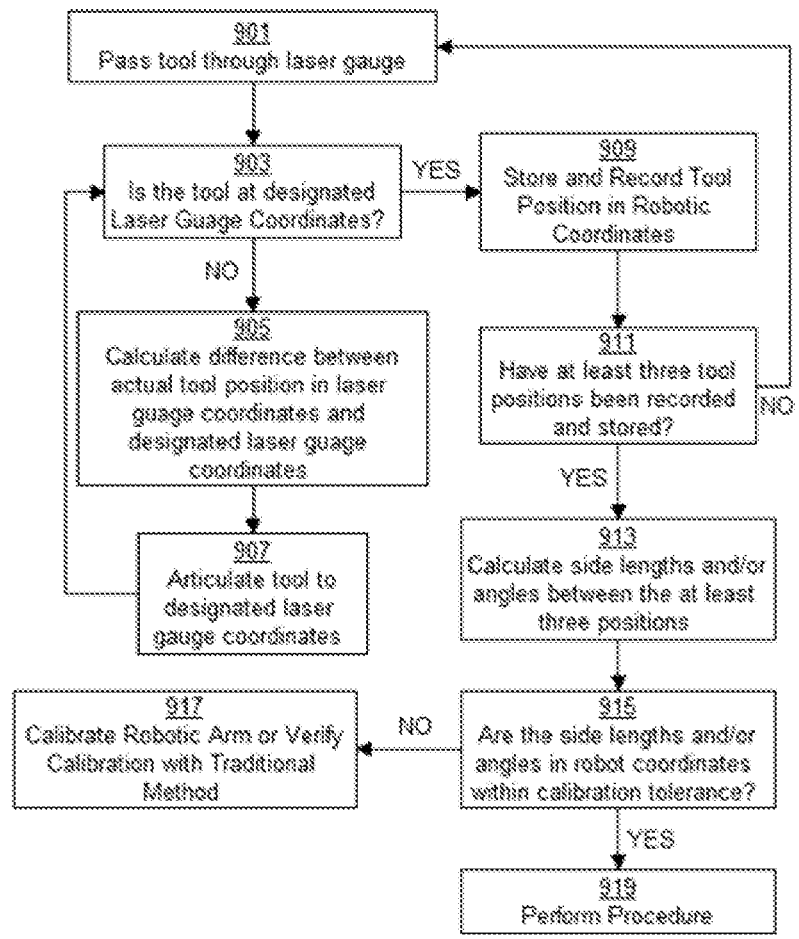
FIG. 9 is an illustrative flowchart of performing a robotic calibration verification in accordance with embodiments of the invention.

In specific inventive embodiments, with reference to FIG. 9, the robot 101 may be initially calibrated by the manufacturer at a customer's site to ensure all of the kinematic parameters are updated for any future use of the robot. The tool 107 may then be passed, either automatically, semi-automatically or manually, through the measuring void 211 of the laser gauge 201 (Block 901). The hardware/software may be programmed or store at least three designated laser gauge coordinate positions. The designated laser gauge coordinates refer to 'x' and 'y' positions within the measuring void coordinates. For example, the hardware/software may store positions such as (1, 1), (5, 5) and (7, 3) corresponding to the positions that may be recorded by the 'x' optical micrometer beam 215 and the 'y' optical micrometer beam 213 ('x', 'y'). The robot 101 may know the general position/orientation (within a few millimeters) of the laser gauge 201 attached to the robot 101. The robot may automatically pass the tool 107 through the laser gauge 201 to the first stored designated laser gauge coordinate. The optical micrometers may then measure the position of the tool 107 within the measuring void 211 and determine if the actual tool position matches the stored designated laser gauge coordinate (Block 903). If the tool position does not match the stored laser gauge coordinate position, then the difference between:

1. the actual tool location measured within the measuring void 211, and
2. the stored designated laser gauge coordinate may be calculated (Block 905). The robot may then articulate the tool 107 to the stored laser gauge coordinates (Block 907) using the calculated difference (e.g., a vector and magnitude from the calculated difference). It should be appreciated that other searching algorithms to articulate the tool 107 to the stored laser gauge coordinate position may be similarly used. For example, the robot 101 may articulate the tool 107 within the measuring void 211 that may continuously minimize the difference between the two locations until a match or best match is achieved. Once the actual position of the tool 107 as measured by the optical micrometers matches or best matches that of the stored designated laser gauge coordinate, the hardware/software may then record and store the position and/or orientation of the tool 107 and/or robot joints/links 105 in robot coordinates (Block 909) using the forward kinematics. The hardware/software may perform this procedure until three different positions/orientations have been recorded and stored in robot coordinates (Block 911). The hardware/software may then calculate the side lengths and/or angles between the three stored coordinates (Block 913) as previously described. If the side lengths and/or angles match or are within the calibration tolerance from a previous calibration using this method (Block 915), then the calibration has been verified and the procedure may be performed (Block 919). If however, the side lengths and/or angles do not match what is expected from the previous calibration, then the system may require maintenance or a traditional calibration technique should be performed (Block 917).

Additional Coordinate Information

Furthermore, in a specific inventive embodiment, a 'z' location of the tool tip 108 may be optionally and/or additionally accounted for by utilizing a method that passes the tool tip 108 back and forth through the measuring void 211. For example, if the tool tip 108 is a sphere as described with respect to FIG. 4, the robot may articulate the tool tip 108 through the second optical micrometer until the actual or a maximum diameter of the sphere is measured. This indicates the center of the sphere. The robot may then articulate the tool tip 108 away from the second optical micrometer until the first optical micrometer measures the actual and/or a maximum diameter. This also indicates the center of the sphere. Subsequently, by knowing where both optical micrometers register the center of the sphere, the robot may then articulate the tool tip 108 directly between the two optical micrometers (i.e., within the gap 206 of the optical micrometers) to obtain a repeatable 'z' location. In a particular inventive embodiment, the 'z' location may be determined by positioning the center of the sphere at the actual and/or maximum diameter within the first or second optical micrometer. Therefore a 'z' location may be specified in space and used with the various methods and embodiments described throughout the specification if necessary.

For example, with respect to FIG. 9, once the tool 107 is at the designated 'x' and 'y' locations in laser gauge coordinates, the robot may articulate the tool such that the center of the sphere is within the center of the gap 206. With the tool 107 at the now designated 'x' and 'y' laser gauge positions (Block 903) and the tool tip 108 is at a repeatedly known 'z' location (as just described), the hardware/software may record and store the tool position in robot coordinates (Block 909). Therefore, no matter where the laser gauge 201 may be positioned on the robot 101, three 'x', 'y' and 'z' locations may be stored in robot coordinates, the side lengths and/or angles measured and compared, and the calibration may be verified. However, it may not be necessary to require all three 'x', 'y' and 'z' coordinates to successfully verify the calibration.

Calibration Verification with an Unexpectedly Oriented Tool

Figure 10:
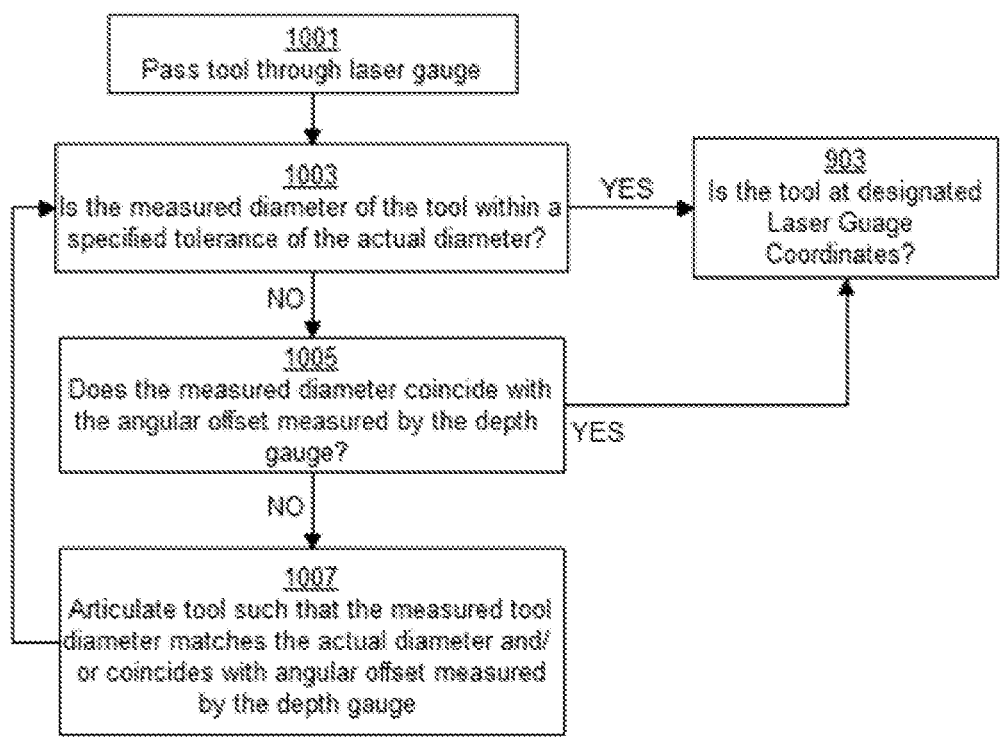
FIG. 10 is an illustrative flowchart of performing a robotic calibration verification with a skewed tool orientation in accordance with embodiments of the invention.

There may be a situation in which the laser gauge 201 is positioned on the robot 101 whereby when passing the tool 107 through the measuring void 211, the measured diameter does not match that of the actual diameter of the tool 107. For example, a cylindrical tool 107 that passes perpendicularly through the measuring void 211 will provide a measurement of the actual diameter of the tool 107 (within a given tolerance). If the optical micrometers measure a larger diameter (i.e., the tool 107 is casting an ellipse on the optical receivers), then the tool 107 may not be oriented perpendicular to the measuring void 211. The depth gauge 601, 607 may be used to calibrate any differences and/or angular offset between the two optical micrometers such that it may be known if the tool 107 is actually oriented incorrectly or if it is a function of the two measuring plane arrangements. Therefore, in a particular inventive embodiment, additional and/or optional steps may be implemented to verify the calibration of the robot 101. With reference to FIG. 10, when the tool 107 is passed through the measuring void 211 of the laser gauge 201 (Block 1001), the diameter of the tool 107 may be measured and compared with the actual known diameter of the tool 107 (Block 1003). If the measured diameter of the tool 107 matches or is within a specified tolerance of the known tool diameter, then the calibration verification process may resume. For example, the hardware/software may determine if the tool 107 is at the designated laser gauge coordinates (Block 903) wherein the remaining steps of FIG. 9 may commence.

However, if the measured diameter of the tool 107 does not match or is outside a specified tolerance of the known tool diameter, then the hardware/software may compare the depth gauge calibration to the measured tool diameter (Block 1005). If, from the depth gauge calibration, it is determined that the optical micrometer planes are actually angularly offset, then a calibration ratio or transformation may be applied to retrieve an accurate reading. The calibration ratio and/or transformation may have been calculated as previously described with the depth gauge 601, 607. If the calibration ratio or transformation then provides a measured tool diameter that matches or is within a specified tolerance of the known diameter, then the calibration verification method may resume (Block 903). If, after applying a calibration ratio or transformation, and the measured tool diameter does not correspond to the actual diameter, then the orientation of the tool 107 is likely skewed. In which case, the hardware/software may articulate the tool 107 such that the measured tool diameter matches and/or coincides with the angular offset of the measured angles determined by the calibration with depth gauges 601 and 607. Once the tool 107 is oriented correctly, any of the methods described herein may be used to verify the calibration. It should be appreciated that the additional and/or optional steps described in FIG. 10 may be used with each of the designated laser gauge coordinates described in FIG. 9, as well as any other procedure outlined in the specification.

The laser gauge 201 and hardware/software may be programmed to perform additional tasks related to the accuracy of the system, including but not limited to tool geometry accuracy verification, transformation matrix accuracy verification, and full robotic calibration verification without the need of any additional external measuring devices. The gap 206 of the laser gauge 201 and sampling rate of the micrometers may be exploited using various methods to obtain additional information about the robotic system and the tools passing through the measuring void 211.

Tool and Digitizer Transformations

In a specific inventive embodiment, certain robotic surgical systems use a digitizer 109 to register the coordinate frame of the anatomy with respect to the coordinate frame of the robotic system. The digitizer may be either mechanically or optically tracked. The coordinate frame of the digitizer probe 110 may need to be known relative to the coordinate frame of the tool tip 108. This may be accomplished by positioning the tip of the digitizer 109 and the robot tool 107 at one or more locations, and then calculating the appropriate transformation matrix. By attaching the digitizer probe 110 to the robotic tool 107 and passing both through the measuring void 211 of the laser gauge 201, a transformation matrix may be created between the coordinate frame of the digitizer 109 and the coordinate frame of the robot 101 from the forward kinematics of digitizer 109 and the robot, respectively.

Similar tools may be used with a spherical tip to calculate the center point of the tool tip 108 as described above. In a particular inventive embodiment, the offset between the digitizer probe tip and the robotic tool tip 108 may be measured by the optical micrometers. The measured offset may then be subtracted, to a common single point in space for both the robotic tool tip position and digitizer probe tip position. If both tips are defined at the same location in space, the coordinate frames of the digitizer 109 may be also calculated and known relative to the coordinate frame of the robot 101. With the known difference between the digitizer tip and the robotic tip 108 and the forward kinematics of the various joints and links, the coordinates may be accurately known relative to one another. Knowing all of the coordinate frames relative to one another other is imperative for performing a precise and accurate medical procedure.

Tool Dimension and Installation Verification

Figures 8A, 8B:
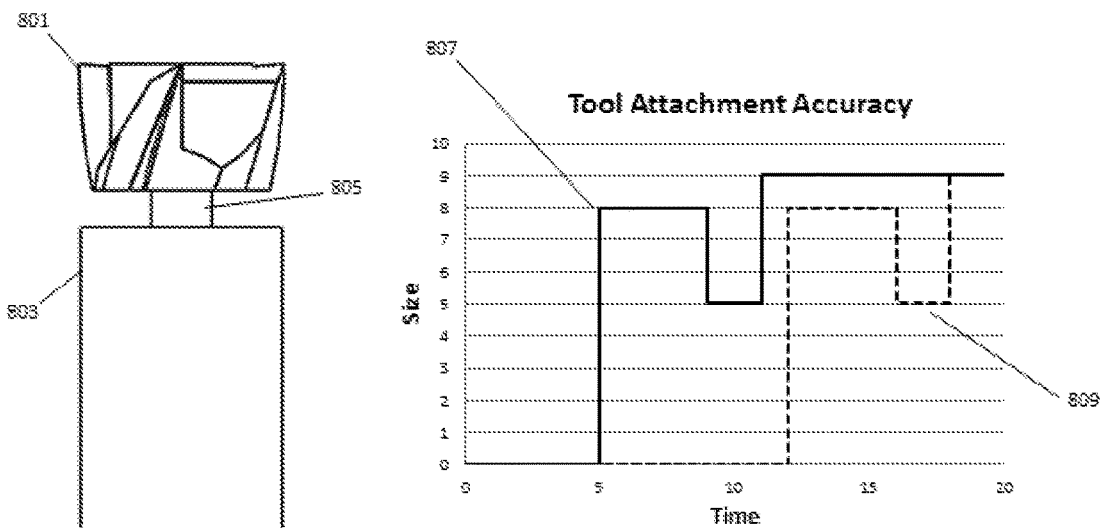
FIG. 8A is a side view of a bone cutting tool with a gap between the cutter and sleeve.
FIG. 8B is a graph of the tool profile of FIG. 8A over time in accordance with an embodiment of the invention.

In many robotic systems, the tool 107 must be attached precisely on the robot 101 such that the geometry of the tool 107 is accurately described and known by the robot computer. For example, with respect to FIG. 8A, a cutter 801 that cuts bone is assembled in a sleeve 803 that is attached to the robotic arm. A small tool gap 805 between the cutter and sleeve is measured using a go no-go gauge. If the tool gap 805 is too large or too small then the cutter may not been properly installed into the sleeve. By measuring the size of the tool gap 805 using the laser gauge 201, a quick and easy contactless method may be provided to ensure the cutter is properly installed. By sampling the size of the tool 107 as it passes through the laser gauge 201, the tool gap 805 is measured. As shown in FIG. 8B, the tool profile is measured vs. time as it passes through a first micrometer 807 and then the second micrometer 809. If the size of the tool gap 805 is in an allowable limit, then the procedure can continue. If the tool gap 805 is too large or small, then a prompt or indicator on the robot can notify the user that the cutter has not been properly installed.

Full Robotic Calibration

In specific inventive embodiments, a full calibration of the robotic arm may also be achieved using the laser gauge 201. Generally, full calibration involves the robotic arm locating points in space at different positions and orientations (POSES). By using a method of locating one or more points within the measuring void 211 at various robotic poses, the errors in locating those points at the different POSES may be used to update the kinematic parameters for full calibration. For example, since the two measuring planes have been calibrated relative to one another, the angle of a tool 107 entering the measuring void 211 can be accurately determined. Based on the angle the tool 107 enters the measuring void 211, the width measurement of either optical micrometer will change. As the angle of the tool 107 increases from normal to the measuring plane, the width measurement of the optical micrometer increases. A relationship between the width measurements of the tool 107 and the angle of the tool 107 can be generated such that the actual angle of the tool 107 can be calculated and compared to the angle the robot has oriented the tool 107. Therefore, the robot can place the end-effector into the measuring void 211 at various POSES to update the kinematic parameters appropriately.

Additionally, due to the high sampling rate of the micrometers, the time it takes for the tool 107 to break both planes may be recorded. The tool 107 may be programmed to pass through the laser gauge 201 at 'x' mm/s. The micrometers may begin taking measurements prior to the tool 107 passing the first measuring plane. The robot computer may then record the time required for the tool tip 108 to break both planes at the designated velocity. The elapsed time is recorded and stored within the robot computer (Block 405). By using velocity, time, and the laser gauge 201, a robot may be calibrated within its encoder limits. For example, an encoder may only have a resolution of measuring within 'n' units, but using the high sampling rate of the micrometers, the robot may be calibrated with a resolution well below 'n' units.

Robot Function and Maintenance

In a specific inventive embodiment, the laser gauge 201 may be used to monitor the functional state of the robot. By passing and abruptly halting a tool 107 within the laser gauge 201, a profile can be created that may represent how the robot components are functioning. When the tool 107 is abruptly halted, vibrations from the tool 107 are recorded by the micrometers. The vibration may have a specific profile that corresponds to the robustness of the system. If over time, the profile begins to change in form or deviate from previous profiles, this may indicate for example, that, the belts in the system are becoming worn, the motors are not functioning properly, the encoders may need to be updated, as well as any other component that may need to be fixed or replaced. Therefore the system itself can check if any required maintenance or calibration is required well before the actual components requires replacement.

Likewise, the operating parameters and functional state may be monitored by tracing specific shapes within the measuring void 211. After the robot is manufactured and calibrated, and the laser-gauge is calibrated, the robot may move the end-effector precisely in a circular shape within the measuring void 211. The shape is stored and used as a comparison to determine how well the robot is functioning over time. After a given number of robotic procedures, the robot may be instructed to reproduce the same circle within the measuring void 211. If the circle matches the circle stored previously, then the robot may be functioning with the same precision as when it first came off the assembly line. However, if there are slight deviations in the traced circle, then the operating parameters or functionality of the robot may be wearing down. For example,the belts may be wearing down, fasteners may be coming lose, the motors may not be driving as well, the kinematic parameters may have drifted, or other parameters may be adversely affecting the performance of the robot. Therefore, by performing the tracing procedure, an early warning sign or signal may be provided to alert a user of a maintenance issue.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

The invention claimed is:

1. An optical gauge for calibration of a robotic arm or a tool attached thereto, said optical gauge comprising:
   a first optical transmitter in communication with a first optical receiver to form a first optical micrometer defining a first direction of planar measurement;
   a second optical transmitter in communication with a second optical receiver to form a second optical micrometer defining a second direction of planar measurement nearly perpendicular to the first direction, said first optical micrometer being offset in a fixed position from said second optical micrometer by a known gap distance in a third direction orthogonal to the first direction and the second direction to create a measurement void with the first direction of planar measurement and the second direction of planar measurement in a space defined between said first optical transmitter and said first optical receiver and between said second optical transmitter and said second optical receiver to obtain calibration data as to position or size of the robotic arm or a tool attached thereto when positioned within or passed through the measurement void; and
   a processor configured to calibrate or verify the calibration of a robot with the calibration data.

2. The optical gauge of claim 1 wherein the first direction of planar measurement is a first plane that measures a first position or a first size of an object in a 'y' axis direction and the second direction of planar measurement is a second plane that measures a second position or a second size of the object in a 'x' axis direction; and wherein a third position or a third size of the object is measured within the measuring void in a 'z' axis direction.

3. The optical gauge of claim 1 wherein said first optical receiver and said second optical receiver are detection devices comprising at least one of photodiodes, CCD cameras, CMOS cameras, magnetic field sensor, or transducers.

4. The optical gauge of claim 1 further comprising a casing to house said first micrometer and said second micrometer for attachment to a robot, where a set of coordinates of said measuring void is known with respect to the robot coordinates.

5. The optical gauge of claim 1 further comprising at least one amplifier connected to at least one of said first micrometer and said second micrometer in communication with a robot.

6. The optical gauge of claim 5 wherein said robot is configured as an autonomous or semi-autonomous robotic system either for medical or industrial applications.

7. The optical gauge of claim 5 wherein said processor or a robot computer performs mathematical operations to obtain a set of additional information about the orientation, velocity, or acceleration of a robotic arm or a tool attached thereto when positioned within or passed through the measurement void.

8. A method for verifying calibration of a robotic arm with the optical gauge of claim 1 comprising:
   performing an initial calibration of said robotic arm;
   passing an end effector of said robotic arm through said measurement void at least once;
   recording and storing from said first micrometer and said second micrometer a position of said end effector within said measuring void; and
   using the recorded position of said end effector from said initial calibration procedure as a comparison tool to verify the robotic arm calibration in a subsequent calibration procedure.

9. A method for verifying calibration of a robotic arm with the optical gauge of claim 1 comprising:
   performing an initial calibration of said robotic arm;
   passing said end effector of said robotic arm through said measurement void three times to obtain three measured positions of said end effector;
   calculating and storing a set of side lengths and a set of angles between the three measured positions in three dimensional space; and
   using the stored set of side lengths and the set of angles from said initial calibration procedure as a comparison tool to verify the robotic arm calibration in a subsequent calibration procedure.

* * * * *